United States Patent
Arguelles

(10) Patent No.: US 7,213,272 B2
(45) Date of Patent: May 8, 2007

(54) URINE COLLECTOR FOR FEMALE USE

(76) Inventor: Francisco Zurita Arguelles, Avda. Carlota Alessandri, 196, 29620 Torremolinos (ES)

( * ) Notice: Subject to any disclaimer, the term of this patent is extended or adjusted under 35 U.S.C. 154(b) by 0 days.

(21) Appl. No.: 10/535,564

(22) PCT Filed: Jan. 20, 2004

(86) PCT No.: PCT/ES2004/000023

§ 371 (c)(1),
(2), (4) Date: May 19, 2005

(87) PCT Pub. No.: WO2004/108027

PCT Pub. Date: Dec. 16, 2004

(65) Prior Publication Data

US 2006/0005307 A1    Jan. 12, 2006

(30) Foreign Application Priority Data

Jun. 6, 2003    (ES) .......................... 200301394 U

(51) Int. Cl.
A47K 11/00    (2006.01)

(52) U.S. Cl. ......................................... 4/144.1; 4/144.4
(58) Field of Classification Search ...... 4/144.1–144.4; 600/574; 604/329
See application file for complete search history.

(56) References Cited

U.S. PATENT DOCUMENTS

| 4,531,245 A | * | 7/1985 | Lowd et al. ................. 4/144.3 |
| 4,756,029 A | * | 7/1988 | Zieve et al. ................. 4/144.4 |
| 4,936,838 A | * | 6/1990 | Cross et al. ................ 604/329 |
| 6,551,292 B1 | * | 4/2003 | D'Acchioli et al. ........ 604/329 |
| 2002/0193760 A1 | * | 12/2002 | Thompson .................. 604/318 |

* cited by examiner

Primary Examiner—Gregory L. Huson
Assistant Examiner—Kristie A. Mahone
(74) Attorney, Agent, or Firm—Collen IP; Donald J. Ranft

(57) ABSTRACT

This invention relates to an improved urine collector for female use. The inventive collector comprises a body which is triangular in plan and which is made from an elastomer material. The body includes a hollow area in the central portion with a projection and valve. The invesntion further comprises a tubular conduit in the hollow area and a bellows in the wall of the hollow area. A recess is provided with two lateral tongue elements separated by a space.

1 Claim, 1 Drawing Sheet

URINE COLLECTOR FOR FEMALE USE

OBJECT OF THE INVENTION

The present specification refers to a Utility Model application corresponding to an improved urine collector for female use, having the purpose of being configured as a body obtained from elastomer materials having a configuration suitable for being adapted to the outer perimetral zone of the urinary organ of a female user, having a tongue element provided with two projections between which there is a recessed zone allowing its adhesion on the perineum of the user, leaving the anus completely free, the tongue element being die-cut for the purpose of being effectively adapted on the irregularities of the skin and being able to be bent on the folds or on deformations which the surface of the skin may have, having on the end of the cavity adjacent to the collector element a series of folds defining the existence of a flexible zone, achieving that when the urine collector is connected to a cannula and a potential stretching occurs, the bellows is also stretched and the urine collector undergoes no pulling that may provoke the separation thereof from the body of the user.

FIELD OF THE INVENTION

This invention is applicable within the industry dedicated to the manufacture of urine collector elements, equipment and devices for temporarily or permanently bedridden patients.

BACKGROUND OF THE INVENTION

The applicant is aware of the current existence of a Utility Model filed in Spain with number 200200220 relating to a urine collector for female use.

In accordance with the configuration thereof and without detracting from any of the substantial features of the invention, it has been verified that this collector protected in said Utility Model, in accordance with the shape of the tongue element, partially covers the anus in its application, and when a cannula is incorporated on the urine collector conduit, it may in turn cause the accidental pulling of the body of the collector, separating it from the fixing surface.

DESCRIPTION OF THE INVENTION

The improved urine collector for female use proposed by the invention has a general configuration that is notably suitable for preventing both the covering of the anus of the user and the pulling thereof should a cannula be fixed on the collector.

More specifically, the improved urine collector for female use object of the invention is formed from a body made from an elastomer material adopting a plan shape similar to a triangle, a central recess being arranged on the narrower end for the purpose of passing over the anus or freeing it from being covered, remaining adhered to the perineum of the user.

Said tongue element is die-cut so that this zone suitably adapts to the irregularities of the skin and at the same time can be bent on the folds or deformations that the skin may have.

The invention is provided with a tubular projection of increasing width configured as the outlet or zone for the passing of the urine towards the direct collector thereof, to which end incorporated in the invention in the upper zone of the tubular projection is an area shaped like a non-rigid bellows or folds, achieving that when a cannula is connected on the collector, and specifically on the tubular zone, possible pulling is avoided, and if so required the bellows stretches, and accordingly the general collector cannot come loose from the zone for the fixing thereof on the body of the user.

DESCRIPTION OF THE DRAWINGS

To complement the description being made and for the purpose of helping to better understand the features of the invention, a set of drawings is attached to the present specification as an integral part thereof, wherein the following is shown with an illustrative and non-limiting character.

PREFERRED EMBODIMENT OF THE INVENTION

Figure 1:
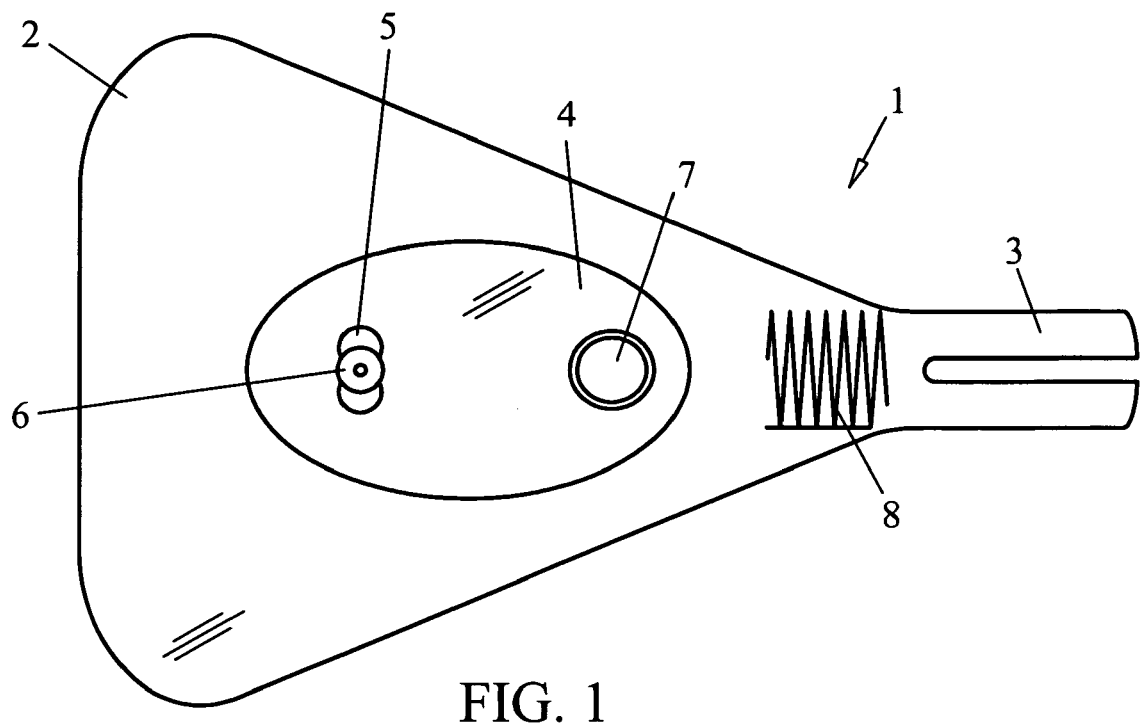
FIG. 1 shows a plan view of the object of the invention corresponding to an improved urine collector for female use, the existence of the recess passing over the anus and allowing its fixing on the female perineum being seen in this graphic representation.
Figure 2:
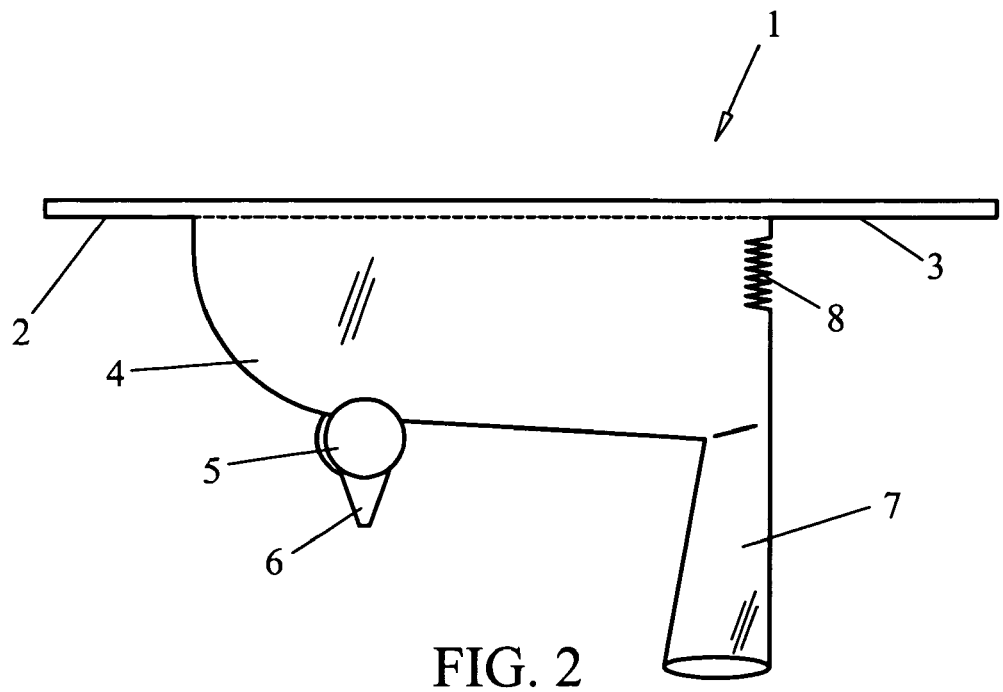
FIG. 2 shows a side elevational view of the object shown in FIG. 1, wherein the existence of the bellows completely or partially preventing the collector from coming loose from the body of the user should a cannula be incorporated, which may cause pulling, can be seen.

In view of these figures, it can be observed how the improved urine collector (1) for female use is formed by a body (2) made from an elastomer material, having a perimetral configuration similar to a triangle with two of these vertexes being rounded. Originating from the third vertex which is the narrow end of the body (2) is recess or flange (3) with two lateral tongue elements and a space extending between them as shown on FIG. 1.

The body (2) includes a hollow or concave area (4) for the collection of urine. This hollow area (4) includes a projection (6) and a valve (5) toward the wide end of the body (2). The hollow area (4) further includes a tubular conduit (7) projecting from the hollow area (4) toward the narrow end of the body (2). Also located in a wall of the hollow area at the narrow end of the body (2) is a bellows-like configuration (8).

The invention claimed is:

1. An improved urine collector for female use, of the type made up of a body (2) made from an elastomer material and adopting a shape that is triangular in plan with two of its three vertexes being rounded;
    a hollow area (4) in the body;
    a recess (3) originating from the third vertex at narrow end of the body with (2) two lateral tongue elements;
    a projection (6) and a valve (5) located in the hollow area (4) toward wider end of body (2);
    a tubular conduit projecting from the hollow area;
    a bellows configuration (8) in a wall of the hollow area (4) at the narrow end of the body (2).

* * * * *